United States Patent [19]

Allenza et al.

[11] Patent Number: 5,008,195
[45] Date of Patent: Apr. 16, 1991

[54] SOME NOVEL PRODUCERS OF CYCLODEXTRIN GLYCOSYLTRANSFERASES

[75] Inventors: Paul Allenza, Bartlett, Ill.; Christy G. Clifft, San Mateo, Calif.; Marie J. Morrell, Des Plaines, Ill.

[73] Assignee: UOP, Des Plaines, Ill.

[21] Appl. No.: 228,411

[22] Filed: Aug. 5, 1988

[51] Int. Cl.$^5$ .......................... C12N 9/10; C12N 1/20; C12N 1/00
[52] U.S. Cl. .................. 435/193; 435/252.5; 435/253.3; 435/832; 435/874
[58] Field of Search .................. 435/193, 252.5, 253.3, 435/832, 874

[56] References Cited

U.S. PATENT DOCUMENTS 3,988,206 10/1976 Shiosaka .......................... 435/193
4,135,977 1/1979 Horikoshi et al. .................. 435/832

FOREIGN PATENT DOCUMENTS 62-269687 11/1987 Japan ................................. 435/832
WO89/01043 2/1989 World Int. Prop. O. .......... 435/832

OTHER PUBLICATIONS

Pongsawasdi et al., "Screening and Identification of a Cyclomaltodextrin Glucanotransferosi-Producing Bacteria", J. Ferment. Technol., vol. 65, No. 4, pp. 463–467, 1987.
J. Szejtli, *Starch,* 34, 379–385 (1982).
H. Bender, *Advances in Biotechnological Processes,* 6, 31, 35 (1986).
Kitahata et al., *Agric. Biol. Chem.,* 47, 1441 (1983).
Nomoto et al., *Agric. Biol. Chem.,* 50, 2701 (1986).
Kato et al., *Agric. Biol. Chem.,* 50, 2161 (1986).

*Primary Examiner*—Douglas W. Robinson
*Assistant Examiner*—Carol M. Geckle
*Attorney, Agent, or Firm*—Thomas K. McBride; Eugene I. Snyder

[57] ABSTRACT

Two Bacillus species and one Pseudomonas species isolated from soil samples showed good cyclodextrin glycosyltransferase activity, even when grown in simple media. The microorganisms are not pH sensitive and grow well in media containing only starch, a nitrogen source, and minerals. All elaborate the desired enzyme within 4 hours of culturing with growth being complete within about 24 hours.

4 Claims, No Drawings

SOME NOVEL PRODUCERS OF CYCLODEXTRIN GLYCOSYLTRANSFERASES

BACKGROUND OF THE INVENTION

Cyclodextrins are cyclic molecules consisting of 1-4 linked alpha-D-glucopyranose monomeric units. The cyclodextrins containing 6-, 7-, and 8-glucose units joined to form a ring, commonly known as alpha-, beta-, and gamma-cyclodextrin, respectively, are the most important cyclodextrins to date, possibly because of their availability relative to cyclodextrins of different ring size. The usefulness of these cyclodextrins arises from their ability to reversibly form inclusion complexes, or clathrates, with many types of compounds. Inclusion complexes arise when a host molecule, such as a cyclodextrin, has a structure containing an interior cavity into which guest molecules can bind by weak interactions such as van der Waal's forces. The latter are short range forces which are sufficiently strong to allow the formation of definite, generally solid complexes, but are sufficiently weak to permit ready dissociation of the complex to a host and guest molecule.

The cyclodextrins are doughnut-shaped molecules with an interior cavity whose size and shape is determined by the number of glucose units that make up the ring. In alpha-cyclodextrin the almost cylindrical cavity is approximately 7 angstroms deep and 5 angstroms in diameter. In beta-cyclodextrin the depth is the same but the diameter is 7 angstroms, and in gamma-cyclodextrin cavity is again 7 angstroms deep but is 9 angstroms in diameter. Cyclodextrins are soluble in water because of the many hydroxyl groups of the glucose subunits that surround the rim of the cavity. However, the interior of the cavities themselves is hydrophobic, and these hydrophobic cavities extract organic molecules from aqueous solution if the organic materials have the correct shape and hydrophobic character.

The complexing ability of cyclodextrins lends itself to various uses. For example, the cyclodextrins are used in encapsulating desirable flavors and fragrances which can then be stored for reasonably long periods of time and added to foods at their preparation. Reciprocally, cyclodextrins may be used in removing undesirable flavors and fragrances from food by complexing with them. Cyclodextrins also are used in the protection of foods against oxidation, photochemical degradation, and thermal decomposition. These and other uses have been summarized by J. Szejtli, Starch, 34, 379–385 (1982)

Commercial utilization of cyclodextrins has been impeded by their relatively high cost resulting from current process limitations. Cyclodextrins generally are formed in relatively poor yield from starch. The necessity of using feedstocks with a relatively low solids content further limits productivity and affords a dilute solution of cyclodextrins which additionally complicates their isolation. Although a method of enhancing cyclodextrin production as recently described in Ser. No. 36,725 ameliorates the cost somewhat, there remain limitations associated with the enzyme itself.

In particular, although cyclodextrin glycosyltransferases are available from several sources, apparently that from *Bacillus circulans* finds greatest commercial use. However, this particular source of the enzyme is unsatisfactory in many regards. Perhaps its greatest disadvantage is that a complex, expensive medium is needed for its adequate growth and enzyme production, although this is not its sole disadvantage.

The inadequacies of known microorganisms as cyclodextrin glycosyltransferase producers was the incentive for our seeking a microorganism which would prove superior. The criteria which needed to be satisfied by a microorganism were decided upon by pragmatic considerations relating to the cost and ease of enzyme production. Among the characteristics sought in the microorganism is rapid growth in simple media. The microorganism also was required to produce high levels of enzyme extracellularly over a broad pH range, which translates to relative insensitivity of enzyme production to changing culture conditions. It also was necessary that the enzyme be produced under conditions where it could be easily separated and purified.

In this application are described a trio of cyclodextrin glycosyltransferase producers isolated from different soil samples. Two are bacilli each elaborating an enzyme producing largely $\beta$-cyclodextrin. The remaining microorganism is gram negative and elaborates an enzyme producing comparable amounts of both $\alpha$- and $\beta$-cyclodextrin. Differences in the phenomenological characteristics of cyclodextrin glycosyltransferases are well known, with enzymes appearing to fall in one of the foregoing two classes. The microorganisms described herein grow quite well on very simple, inexpensive media, are relatively insensitive to pH of the medium, and show good enzyme production at an early growth stage even in simple media. Since enzyme production is recognized as being responsive to changes in the growth medium, it will be appreciated that the enzyme production levels referred to herein are not optimized and may represent only a fraction of that which the microorganism is capable of producing under optimum conditions.

The sensitivity of some of the prior art cyclodextrin glycosyltransferase producers to growth medium pH is well documented. Among the outstanding successes of our invention is achievement of our goal to find such producers having the ability to grow well over a relatively broad range of pH and to grow rapidly even in simple media.

SUMMARY OF THE INVENTION

A purpose of this invention is to obtain biologically pure cultures of microorganisms which produce substantial amounts of readily recoverable cyclodextrin glycosyltransferase and which grow rapidly in simple growth media over a wide pH range. An embodiment is a Bacillus sp. NRRL B-18373. Another embodiment is a second Bacillus sp. NRRL B-18374. Still another embodiment is a Pseudomonas sp. NRRL B-18375.

DESCRIPTION OF THE INVENTION

In his review, Bender lists 8 cyclodextrin glycosyltransferase-producing microorganisms, 6 of which are Bacillus species. H. Bender, Advances in Biotechnological Processes, 6, 31, 35 (1986). As Bender recognized and stated, complex nutrient media-containing soluble starches, corn steep liquor, wheat bran, dry yeast or yeast extract, soy beam meal, casein peptone or meat extracts, in addition to inorganic salts-were used for cultivation. Since then Kitahata et al., Agric. Biol. Chem., 47, 1441 (1983) has described cyclodextrinase from *Bacillus coagulans* whose growth and enzyme production also required a complex and expensive growth medium. Nomoto and coworkers isolated a strain of alkalophilic Bacillus sp. HA3-3-2 which showed cyclodextrin glycosyltransferase activity in the culture broth, Agric. Biol. Chem., 50, 2701 (1986). This strain also required a complex medium for growth and enzyme production. Finally, Kato and Horikoshi, Agric. Biol. Chem., 50, 2161 (1986) refers to a *Bacillus subtilis* that also is a cyclodextrin glycosyltransferase producer without elaborating further on the microorganism other than to characterize its enzyme as one forming gamma-cyclodextrin predominantly.

We have obtained pure cultures of several microorganisms isolated as part of a screening program for bacteria having cyclodextrin glycosyltransferase activity. Our screening program can be summarized as follows. Microorganisms showing some desirable enzymatic activities were grown as biologically pure cultures. These cultures were then assayed for cyclodextrin glycosyltransferase activity, and those exhibiting less than 500 KI units per mL of enzyme activity were not further examined. Cyclodextrin glycosyltransferase activity was then determined for the remaining microorganisms in a manner more specific for cyclodextrin-forming activity, and several promising strains were selected. The biologically pure cultures described herein are capable of producing a recoverable amount of cyclodextrin glycosyltransferase when grown between about 20° and about 45° C. in a simple medium containing only starch, a nitrogen source, and minerals.

MICROBIAL SOURCES

Soil and water samples from a variety of locations were used as the source of bacterial producers of cyclodextrinase. Among these were soil samples from a garden plot and a corn field in Des Plaines, Ill.; a garden plot in Mt. Prospect, Ill. and Park Forest, Ill.; a 10 foot excavation pit and a garden plot in Bartlett, Ill.; two corn fields near Des Moines, Iowa; soil near a decaying cactus in Arizona; a field in San Mateo, Calif.; and from a pumpkin farm in Half Moon Bay, Calif. Pond water was obtained from a pond in Mt. Prospect, Ill., and Des Plaines, Ill. and sewage sludge was from an Illinois municipal sewage treatment plant. For each of the soil samples approximately 2–5 grams of soil was added to 10 mL of sterile distilled water and vigorously mixed. After allowing the sample to settle for a few minutes, the cloudy suspension was used for inoculation of cultures.

CULTURE ISOLATION

Cultures from numerous water and soil samples were grown. Those showing some cyclodextrin glycosyltransferase activity were streaked for isolation on a non-selective starch agar medium. Most strains grew rapidly on this medium and several transfers could be made if necessary to obtain axenic cultures. Pure cultures were maintained on starch agar and were lyophilized for long-term storage.

SCREENING OF ISOLATES

Pure cultures which were isolated by the above procedure were screened for cyclodextrinase activity in the following manner. First the bacteria were inoculated to 50 mL of medium containing starch as the sole carbon source. These cultures were incubated at 30° C. with shaking until fully grown, usually 26 to 48 hours. At this point the optical density at 600 nm was recorded and a 1.0 mL sample was removed and placed in a 1.5 mL eppindorff tube and centrifuged for 2 to 3 minutes to pellet the cells. The supernatant was used as a presumptive source of enzyme to perform a KI assay (see below). This assay identifies starch liquifying activity and serves as an initial screen for cyclodextrinase (a specific type of starch degrading enzyme). Cultures exhibiting KI activity (generally 500 units per mL was used as the minimum) were used to inoculate a 200 mL culture of the same starch defined medium. When this culture was fully grown again a 1 mL sample was taken and the KI assay verified and the starch degrading activity determined more precisely.

The free enzyme KI assay procedure for cyclodextrinase used as a substrate 0.2% soluble starch containing 5 mM CaCl$_2$ and 100 mM imidazole at pH 7.0. To 0.30 mL of the substrate at 40° C. was added 10 µl of enzyme. After 10 minutes of mixing the reaction was quenched with 4.0 mL of 0.2M HCl, and 0.5 mL of a solution containing 0.02% I$_2$ and 0.20% KI was added. The background control was prepared by adding to 0.30 mL of the substrate 4.0 mL of 0.2M HCl followed by 10 µl enzyme and 0.5 mL of the I$_2$-KI mixture. The activity, in units per mL, was determined from the equation, $$\text{activity(units/mL)} = \frac{OD_B - OD_S}{[0.01 \times OD_B]} \cdot \times 100$$

where $OD_B$ and $OD_S$ is the optical density at 700 nanometers of the background (control) and sample, respectively. The difference in optical density between the background and the sample must be between 0.1 and 0.4 absorbance units, representing activities between 1250 and 5000 units per mL. If values are not within this range, dilutions must be made to the enzyme and then factored into the calculation.

In order to determine cyclodextrinase activity a partial purification of the enzyme was necessary since the crude supernatant preparation tended to foul HPLC columns. The partial purification involved first centrifuging 200 mL culture at 8000 rpm to remove cells. In a beaker, 40 g of (NH$_4$)$_2$SO$_4$ was slowly added to the culture supernatant and the solution was stirred for about 10 minutes. Next 10 g of insoluble pearl starch was slowly added and the suspension was stirred for about 30 minutes. The insoluble starch (containing the bound cyclodextrinase) was collected by filtration on a crepe filter paper using a buchner funnel. Once the filter cake was air dried the starch was added to 30 mL of a solution containing 10 mM K$_2$HPO$_4$, 3M NaCl and 0.1M maltose at pH 7.5 and allowed to stir at room temperature for 30 to 45 minutes. This solution was next filtered to remove the starch and then filtered again through filters of decreasing porosity until a clear solution was obtained. In later enzyme purifications the volumes of the culture and all solutions were decreased fourfold in order to handle the purification of several enzyme preparations at once. In either case, the maltose and NaCl were removed from the final solution by dialysis for 24 hours against 100 volumes of a solution containing 5 mM glycine and 5 mM CaCl$_2$. This enzyme preparation was then stored at 4° C. in a sterile vial until use. In most cases the assay of cyclodextrinase activity for the semipurified enzyme samples was performed immediately.

ASSAY OF CYCLODEXTRINASE ACTIVITY

To determine the actual presence of cyclodextrinase activity as opposed to starch liquifying activity, an assay was performed in which the cyclodextrin product is measured by HPLC. For this assay 100 μl of the purified enzyme preparation was added to 2 mL of a 2% solution of Maltrin 150, 5 mM $CaCl_2$, and 5 mM glycine at pH 7. The assay mixture was incubated at 40° C. for 2 hours. At this point 40 μl of an alpha amylase/glucoamylase solution (prepared by addition of 5 mL pure glucoamylase with 20 mg of bacterial alpha amylase to 45 mL of 0.1M acetate buffer at pH 4.2) was added and the entire solution drawn up into a 3 cc syringe. The syringe was sealed and incubated at 60° C. for 1 hour and then placed in boiling water for 2 minutes. Once cooled, the sample was filtered through a 0.2 μm filter and sent for HPLC analysis for the quantitative identification of alpha, beta and gamma cyclodextrins.

CHARACTERIZATION OF ISOLATES

Three of the most promising isolates were designated as strains 170, 430 and 860. The former is a gram negative bacterium tentatively identified as a Pseudomonas species which is not aeruginosa, putida or fluorescens. This microorganism was further characterized as described in Table 1.

TABLE 1

| Selected Characteristics of Strain 170 |
| --- |
| Gram negative staining reaction |
| Small rod |
| Oxidase positive |
| Catalase positive |
| No anaerobic fermentation of dextrose |
| No decarboxylation of arginine |
| Nitrogen gas not produced |
| Hydrogen sulfide not produced |
| Indole not produced |
| Xylose not utilized |
| Dextrose not utilized |
| Urea not hydrolyzed |
| Citrate is utilized |

This strain also grows well under standard conditions and produces high levels of cyclodextrinase enzyme which is readily purified. The enzyme is active over the pH range tested (pH 5.9 to 8.8) with a higher level of activity apparent at the more acid pH values. Both alpha and beta cyclodextrins are produced from starch.

Strains 430 and 860 were both Bacilli which were typed typed by ATCC, with results summarized in Table 2. Each isolate was characterized according to the methods of Ruth Gordon et al., USDA Handbook No. 42, the Genus Bacillus. It was reported that each isolate differed in significant characteristics from recognized species of Bacillus.

TABLE 2

| Characterization of Strains 430 and 860 | | |
| --- | --- | --- |
|  | 430 | 860 |
| Rods | + | + |
| Rods Straight | + | + |
| Rods Curved | − | − |
| Length 2.1–3.0 μ | + | + |
| Length 3.1–4.0 μ | + | + |
| Length 4.1–5.0 μ | − | − |
| Length 5.0–10.0 μ | − | − |
| Width under 0.5 μ | − | − |
| Width 0.5–1.0 μ | + | + |
| Width 1.1–2.0 μ | +/− | +/− |
| Cells single | + | + |
| Cells chained | − | − |
| Ends Tapered | − | − |
| Ends Rounded | + | + |
| Ends Squared | − | − |
| Endospore Formed | + | +· |
| Sporang Swollen | − | − |
| One Spore/cell | + | + |
| Spore Round | − | − |
| Spore Cylindrical | + | + |
| Spore Oval | + | + |
| Spore Central | + | − |
| Spore Terminal | − | − |
| Spore Subterminal | + | + |
| Parasporal Crystal | − | − |
| Gram Stained | + | + |
| Gram Positive | − | − |
| Gram negative | + | + |
| Gram variable | − | − |
| Colony translucent | + | + |
| Colony transparent | − | − |
| Colony opaque | (D)W | (D)W |
| Colony Entire | + | + |
| Colony erose | − | (D)+ |
| Colony rhizoid | − | − |
| Colony irregular | − | − |
| Colony lobate | (D)+ | − |
| Colony low convex | + | + |
| Colony high convex | − | − |
| Colony convuluted | − | − |
| Colony Flat | − | − |
| Colony Raised | − | − |
| Colony moves as unit | − | − |
| Colony disassociates | − | − |
| Colony glistening | + | + |
| Colony dull | − | − |
| Colony dry | − | − |
| Colony smooth | + | + |
| Colony rough | − | − |
| Sol. brown pigment | − | − |
| Sol. black pigment | − | − |
| Sol. yellow pigment | − | − |
| Insol. brown pigment | − | − |
| Insol. black pigment | − | − |
| Insol. yellow pigment | − | − |
| Insol. orange pigment | − | − |
| Insol. red pigment | − | − |
| Cells motile | + | + |
| Motile, flagella | + | + |
| Peritrichous | + | + |
| Opt. temp. 0–10° C. | − | − |
| Opt. temp. 11–20° C. | − | − |
| Opt. temp. 21–30° C. | + | + |
| Opt. temp. 31–40° C. | − | − |
| Opt. temp. 41–50° C. | − | − |
| Opt. temp. 51–60° C. | − | − |
| Growth at 30° C. | + | + |
| Growth at 37° C. | + | + |
| Growth at 45° C. | + | + |
| Growth at 50° C. | − | − |
| Growth at 55° C. | − | − |
| Growth at 60° C. | − | − |
| Growth at 65° C. | − | − |
| Growth at 70° C. | − | − |
| Growth in 5% NaCl | − | − |
| Growth in 7% NaCl | − | − |
| Growth in 10% NaCl | − | − |
| Acid from L-arabinose | + | + |
| Acid delayed >14 days | − | − |
| Gas from L-arabinose | − | − |
| Acid from D-xylose | + | + |
| Acid delayed >14 days | − | − |
| Gas from D-xylose | − | − |
| Acid from D-glucose | + | + |
| Acid delayed >14 days | − | − |
| Gas from D-glucose | − | − |
| Acid from lactose | + | + |
| Acid delayed >14 days | − | − |
| Gas from lactose | − | − |
| Acid from sucrose | + | + |

TABLE 2-continued

Characterization of Strains 430 and 860

| | 430 | 860 |
|---|---|---|
| Acid delayed >14 days | − | − |
| Gas from sucrose | − | − |
| Acid from D-mannitol | + | + |
| Acid delayed >14 days | − | − |
| Gas from D-mannitol | − | − |
| Propionate utilization | − | − |
| Citrate utilization | − | − |
| Hippurate hydrolysis | − | − |
| Polysaccharide hydrol. | + | + |
| Starch hydrolyzed | + | + |
| Gelatin liquified | + | + |
| Casein hydrolysed | − | − |
| Methylene blue reduced | + | + |
| Methylene blue reoxid. | + | + |
| Nitrate reduced | + | + |
| $NO_3$ reduced to $NO_2$ | + | + |
| Nitrate reduced | − | − |
| $NO_3$ reduced to $NO_2$ | − | − |
| VP(5198) positive | *+ | TR |
| VP(5198 fil) positive | *+ | TR |
| VP (5331) positive | *+ | − |
| $H_2O_2$ decomposed | + | + |
| Indole | − | − |
| Tryosine decomposed | − | − |
| Dihydroxyacetone | − | − |
| Litmus milk acid | + | + |
| Litmus milk coagulated | − | − |
| Litmus milk alkaline | − | − |
| Litmus milk peptonized | − | − |
| Litmus milk reduced | + | + |
| Growth at pH 6.0 | + | + |
| Growth at pH 5.7 | + | + |
| ph VP 5198 6.0 or less | + | + |
| ph VP 5198 7.0 ± 0.5 | − | − |
| ph VP 5198 8.0 or more | − | − |
| Aerobe (obligate) | − | − |
| Facultative | + | + |
| Microaerophil | − | − |
| Anaerobe | − | − |
| Growth in 0.02% azide | − | − |
| Gas from sealed nitrate | − | − |
| Growth in sealed glucose | + | + |
| Lecithinase | + | − |

\* = Moderate reaction scored as positive
TR = Trace score as negative
D = Delayed Each of the aforementioned strains grew well in a simple medium consisting of 1% soluble starch, 0.4 µg/mL biotin, 40 µg/mL thiamin (both of which can be substituted by 0.01% yeast extract), citric acid (1.6 mM), and a salt mixture containing magnesium sulfate (4 mM), manganese sulfate (0.03 mM), ferrous sulfate (0.06 mM), sodium chloride (6.8 mM), potassium acid phosphate (14.6 mM), calcium chloride (1 mM), ammonium chloride (10 mM), ammonium sulfate (0.06 mM) and potassium chloride (5.4 mM) initially at pH 7. However, no pH adjustment was necessary during growth even though the pH declined to about 5.5. In all cases the growth period needed before cyclodextrin glycosyltransferase activity was observed was approximately 4 hours, which compares to an induction period of 15-20 hours for Bacillus sp. 38-2, and growth was complete within 24 hours. There was maximum enzyme production during the stationary phase. Some characteristics of these microorganisms as regards cyclodextrinase production and some characteristics of the free enzyme are summarized in Table 3.

TABLE 3

Bacterial Producers of Cyclodextrinase

| | 170 | 430 | 860 |
|---|---|---|---|
| Enzyme Production (KU/ml) | 35 | 7 | 4 |
| Relative CD Yield | | | |
| alpha | 40 | 18 | 22 |
| beta | 60 | 82 | 78 |
| gamma | — | — | — |
| Maximum Conversion | 17% | 22% | 19% |

What is claimed is:

1. A biologically pure culture of a Bacillus sp. NRRL B-18373, said culture being capable of producing in a nutrient medium containing only starch, a nitrogen source, and minerals, a recoverable amount of a cyclodextrin glycosyltransferase.

2. A biologically pure culture of a Bacillus sp. NRRL B-18374, said culture being capable of producing in a nutrient medium containing only starch, a nitrogen source, and minerals, a recoverable amount of a cyclodextrin glycosyltransferase.

3. A biologically pure culture of Pseudomonas sp. NRRL B-18375, said culture being capable of producing in a nutrient medium containing only starch, a nitrogen source, and minerals, a recoverable amount of a cyclodextrin glycosyltransferase.

4. A method of producing a cyclodextrin glycosyltransferase comprising growing aerobically Bacillus sp. NRRL B-18373, B-18374 or Pseudomonas sp. NRRL B-18375 in a medium containing an assimilable source of carbon, nitrogen, and mineral nutrients, at a temperature from about 20° to about 45° C., and recovering the cyclodextrin glycosyltransferase produced thereby.

* * * * *